United States Patent
Cattell

(10) Patent No.: US 6,879,915 B2
(45) Date of Patent: Apr. 12, 2005

(54) CHEMICAL ARRAY FABRICATION AND USE

(75) Inventor: Herbert F. Cattell, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 118 days.

(21) Appl. No.: 09/775,387

(22) Filed: Jan. 31, 2001

(65) Prior Publication Data

US 2002/0102559 A1 Aug. 1, 2002

(51) Int. Cl.[7] .................. G06F 19/00; G01N 33/48; G01N 33/50; C12Q 1/68
(52) U.S. Cl. .................. 702/20; 435/6; 422/68.1; 702/19
(58) Field of Search ............... 435/6; 702/19, 702/20; 422/68.1

(56) References Cited

U.S. PATENT DOCUMENTS

| | | | |
|---|---|---|---|
| 5,281,540 A | 1/1994 | Merkh et al. | |
| 5,314,829 A | 5/1994 | Coles | |
| 5,404,523 A | 4/1995 | DellaFera et al. | |
| 5,812,793 A | 9/1998 | Shakib et al. | |
| 5,837,454 A | 11/1998 | Cozzette et al. | |
| 6,215,894 B1 | 4/2001 | Zeleny et al. | |
| 6,406,849 B1 * | 6/2002 | Dorsel et al. | 435/6 |
| 6,470,277 B1 * | 10/2002 | Chin et al. | 702/19 |
| 2002/0055102 A1 * | 5/2002 | Stern | 435/6 |
| 2002/0086319 A1 * | 7/2002 | Ellson et al. | 435/6 |
| 2002/0168639 A1 * | 11/2002 | Muraca | 435/6 |
| 2002/0177135 A1 * | 11/2002 | Doung | 435/6 |

FOREIGN PATENT DOCUMENTS

| | | |
|---|---|---|
| GB | 2319838 | 6/1998 |
| WO | WO 94/05394 | 3/1994 |
| WO | WO 95/33846 | 12/1995 |
| WO | WO 96/18903 | 6/1996 |

* cited by examiner

*Primary Examiner*—Marianne P. Allen
(74) *Attorney, Agent, or Firm*—Gordon Stewart

(57) ABSTRACT

A method of using an addressable array of biopolymers on a substrate includes receiving the addressable array and an associated machine readable identifier carried on an array substrate or array housing. The array is exposed to a sample and read, and the identifier machine read as an identifier signal. Biological function data for one or more of the biopolymers is retrieved from a memory based on the identifier signal. Other methods in which first and updated sets of feature characteristic data may readily be provided to array users, and methods of generating arrays are also provided, as are apparatus and computer program products which can execute a method for generating or using arrays.

14 Claims, 4 Drawing Sheets

CHEMICAL ARRAY FABRICATION AND USE

FIELD OF THE INVENTION

This invention relates to arrays, particularly biopolymer arrays (such polynucleotide arrays, and particularly DNA arrays) which are useful in diagnostic, screening, gene expression analysis, and other applications.

BACKGROUND OF THE INVENTION

Arrays of biopolymers, such as arrays of peptides or polynucleotides (such as DNA or RNA), are known and are used, for example, as diagnostic or screening tools. Such arrays include regions (sometimes referenced as features or spots) of usually different sequence biopolymers arranged in a predetermined configuration on a substrate. The arrays, when exposed to a sample, will exhibit a pattern of binding which is indicative of the presence and/or concentration of one or more components of the sample, such as an antigen in the case of a peptide array or a polynucleotide of particular sequence in the case of a polynucleotide array. The binding pattern can be detected by reading the array, for example, by observing a fluorescence pattern on the array following exposure to a fluid sample in which all potential targets (for example, DNA) in the sample have been labeled with a suitable fluorescent label.

Methods of fabricating biopolymer arrays can be fabricated using light directed methods, in situ synthesis methods or deposition of the previously obtained biopolymers. In known light directed synthesis methods the aim is to form an array of oligonucleotides on a surface by removing a photoremovable group from a surface, coupling a monomer to the exposed region of the surface, and repeating the process. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as iterating the sequence of depositing droplets of: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one iteration so that the different regions of the completed array will have different desired biopolymer sequences. One or more intermediate further steps may be required in each iteration, such as oxidation and washing steps.

The "deposition method" basically involve depositing previously obtained biopolymers at predetermined locations on a substrate which are suitably activated such that the biopolymers can link thereto. The deposited biopolymers may, for example, be obtained from synthetic or biological sources. Biopolymers of different sequence may be deposited at different regions of the substrate to yield the completed array. Washing or other additional steps may also be used. Typical procedures known in the art for deposition of polynucleotides, particularly DNA such as whole oligomers or cDNA, are to load a small volume of DNA in solution in one or more drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into a drop dispenser in the form of an inkjet head and fired onto the substrate. Such a technique has been described, for example, in PCT publications WO 95/25116 and WO 98/41531, and elsewhere. This method has the advantage of non-contact deposition. Still other methods include pipetting and positive displacement pumps such as the Biodot equipment (available from Bio-Dot Inc., Irvine Calif., USA).

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots (features). Due to the precision required, and to maintain costs low, it will often be desirable to have the arrays fabricated at a fabrication facility and then shipped to the end user. The present invention realizes that during the fabrication process small errors may result which do not make a given array useless provided they are communicated to an end user of the array so he can interpret the data obtained from reading an array exposed to a sample accordingly. Such small errors may include, for example, incorrect feature size, complete absence of one feature, or slightly incorrect feature location. However, the present invention further realizes that at any later time following array fabrication one or more previously detected errors in any of the thousands of features on a typical array, may be found. It would be desirable if the nature of such later detected errors could quickly and conveniently be provided to many end users of the different arrays from a central fabrication facility. Furthermore, it would be desirable if later discovered biological function data associated with one or more features of an array could similarly be provided to many end users. The present invention further realizes that when many arrays with the same set of features are provided to many different end users, there is the opportunity for them to discover feature errors or biological function data associated with features which could be advantageously shared with others. It would be desirable then, to provide a means by which array users could quickly and easily obtain the benefit of prior users' discoveries of any quality issues or biological function data associated with array features.

SUMMARY OF THE INVENTION

The present invention then, provides in one aspect a method of using an addressable array of biopolymers (such as polynucleotides, particularly DNA, or peptides) on a substrate. The method includes receiving the addressable array and an associated machine readable identifier carried on an array substrate or array housing. The array may be exposed to a sample and read. Additionally, at any point in this method the identifier may be machine read as an identifier signal. The machine readable identifier may be read while the array is in a same apparatus which reads the array, but this is not required. Biological function data may be retrieved for one or more of the biopolymers from a memory based on the identifier signal. One method for the retrieval of the biological function data includes communicating the identifier signal to a processor which retrieves data on the identity of the biopolymers based on the read identifier. Such biopolymer identity data can be any type of data which distinguishes different biopolymers on the array (for example, biopolymer sequences or molecular weights of different biopolymer fractions obtained from a particular restriction fragment experiment on a particular polynucleotide sample, or that a biopolymer was received from a particular source). The identity data on the biopolymers is communicated to a processor which retrieves the biological function data for one or more of the biopolymers from a memory based on the retrieved identity data. Optionally, the processor which retrieves the biological function data and the memory from which the biological function data is retrieved, may be at a location (such as a central fabrication station) remote from the location at which the array and identifier are read (such as at an end user station). In such case, the read identifier or biopolymer identity data is communicated to the remote location and the biological function data is received in response. Another method for retrieval is from a memory which is a portable storage medium (such as may be received from a remote location).

In the situation where communication with a remote location is used, the method may also include obtaining a communication address of the remote station using the identifier signal. For example, the communication address may be included as part of the identifier or it may be retrieved from a database of communication addresses associated with at least part of respective identifiers. In one example, the database lists the communication address of a particular fabricator which fabricated all arrays with a predetermined portion of an identifier. The communication address so obtained may be used to establish communication with the remote station.

The present invention further provides a method of using an addressable arrays of biopolymers on a substrate which may, for example, be executed at a location sometimes referenced as an end user station. In one aspect, the method includes receiving the addressable arrays with respective associated machine readable identifiers carried on an array substrate or array housing. Each array is exposed to a sample and read. At any stage, the array identifier is machine read as an identifier signal. A first set of feature characteristic data for each array received from a remote location is saved into a memory. An updated set of feature characteristic data for at least some of the features of at least some of the arrays, received from a remote location, is also saved into a memory (which may be the same or different from the memory into which the first set is saved). Either or both of the first and updated sets may be received by communication from a remote location (such as a central fabrication station) in response to receipt at the remote location of a communication of the read array identifier, or received on a portable storage medium. The saved first and updated sets of feature characteristic data for each array is retrieved using the read identifier signal. One way of accomplishing this includes replacing feature characteristic data from the first set for a given feature with corresponding data from the update set when the first set data conflicts with the updated set data.

The method of using may additionally include communicating feature characteristic data for an array to a remote location in association with an identification of the feature (such identification including, for example, the array identifier and feature location within the array, or an identification of the biopolymer at the feature for which characteristic data is communicated). Feature characteristics includes any one or more of feature physical characteristics, for example, an indication of a suspected feature error, and biological function data for one or more of the biopolymers. Examples of suspected feature errors include errors in dimensions (such as total area), location, presence (for example, an expected feature is missing), or amount of biopolymer present at a feature. The method of using may also include communicating feature characteristic data that is not directly used for feature extraction, such as biological function data for one or more features (for example, feature sequence) if previously unknown.

The present invention further provides a method of generating addressable arrays of biopolymers on a substrate. Such a method includes providing the biopolymers for each array on different regions of the substrate so as to fabricate the array with features of different composition. An identifier is applied to the substrate of each array or a housing carrying the substrate, different identifiers being applied for arrays having different sets of features. Data on the identity of the biopolymers on each array in association with the corresponding identifier may optionally be saved into memory. The fabricated arrays and a first set of feature characteristic data associated with at least one array identifier, may be forwarded to multiple different remote locations (such as locations of end users of the array). An updated set of feature characteristic data for an array is also communicated to one or more remote locations (such as a location of an end user of the array) in response to a received communication of the identifier corresponding to that array from a remote location. Alternatively, the updated set of feature characteristics may be forwarded by shipping a portable storage medium carrying the data to the one or more remote locations (such as those locations to which corresponding arrays were shipped) Alternatively or additionally to forwarding first and updated sets, biological function data for one or more of the biopolymers on an array may be forwarded to a remote location (such as by communication in response to a received communication of the identifier for that array).

In one aspect, the method of generating arrays may optionally further include receiving feature characteristic data for an array in association with an identification of the feature, communicated from a remote location (such as an end user). The received feature characteristic data may be for a sub-set of features on a first array and may be received in association with an array identifier corresponding to the first array. The updated set of feature characteristic data communicated to a remote location as previously described, may optionally include the received feature characteristic data for the sub-set of features. In this manner, this aspect of the invention allows, for example, end users to provide feature characteristic data which can be made available from a fabrication station as update data for other remote locations (for example, other end users such as upon receipt from such other end users of a communicated identifier for a first array).

The present invention further provides apparatus which can execute one or more methods of the present invention. In one aspect, for example, an apparatus for using an addressable array of biopolymers on a substrate has an array reader which reads the array following exposure to a sample. A reader (which may be the same or different from the array reader) reads an identifier carried on an array substrate or an array housing, as an identifier signal. A processor is also provided to perform any or all of the steps of a method of the invention, which can be performed by a processor. For example, the processor may retrieve biological function data for one or more of the biopolymers from a memory (such as a portable storage medium in a portable storage medium reader) based on the read identifier signal (such as by retrieving data on the identity of the biopolymers based on the read identifier; and retrieving the biological function data for one or more of the biopolymers from a memory based on the retrieved identity data). As another example, the processor may either control reading of the array or process information obtained from reading the array, in accordance with the retrieved biological function data. The apparatus may further include a communication module through which the processor may perform any communication functions required by the method. As a further example, the processor may retrieve feature characteristic data for the array from a memory based on the read identifier signal, communicate feature characteristic data for the array to a remote location in association with an identification of the feature, and/or additionally obtain a communication address for the remote location using the identifier signal as described above.

In still another aspect of the apparatus, a central fabrication station is provided which includes an array fabricator to provide biopolymers onto different regions of multiple substrates so as to fabricate arrays. A writing system is also included which applies a map identifier to each substrate or a housing carrying the substrate, different identifiers being applied for arrays having different sets of features. The processor in this aspect save into a memory: data on the identity of the biopolymers for each array, in association with the identifier for that array; first sets of feature characteristic data for the arrays each in association with the array identifier; and an updated set of feature characteristic data for at least some of the features of at least some of the arrays, each in association with a corresponding array identifier, which saving occurs at a time later than the saving of the first sets of feature characteristics. One same memory or different memories may be used for saving the foregoing items.

The present invention further provides a computer program product, comprising: a computer readable storage medium having a computer program stored thereon for performing, when loaded into a computer communicating with a suitable apparatus (such as at a fabrication or end user station) will cause execution of any one or more methods of the present invention.

One or more of the various aspects of the present invention may provide one or more of the following, or other, useful benefits. For example, errors detected after array fabrication may quickly and conveniently be provided to many end users of the different arrays from a central fabrication facility. Furthermore, later discovered biological function data associated with one or more features of an array may be provided to many end users. Additionally, there is the opportunity for some users which discover feature errors or biological function data associated with features, to easily share such information with others.

BRIEF DESCRIPTION OF THE DRAWINGS

Embodiments of the invention will now be described with reference to the drawings in which.

To facilitate understanding, identical reference numerals have been used, where practical, to designate identical elements that are common to the figures.

DETAILED DESCRIPTION OF THE INVENTION

Figure 1:
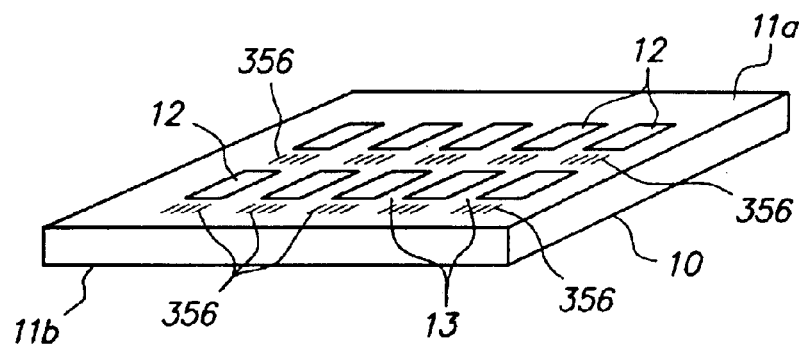
FIG. 1 illustrates a substrate carrying multiple arrays, such as may be fabricated by methods of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides.

An "array", unless a contrary intention appears, includes any one, two or three dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, errors, or some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electric or electromagnetic (including light) signals over a suitable communication channel (for example, a private or public network). "Forwarding" an item refers to any means of getting that item from one location to the next, such as by causing the item to be physically transported (shipped) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. "Fluid" is used herein to reference a liquid. A "set" or a "sub-set" may have one or more members (for example, one or more droplets). A "processor" includes any one or more electrical and/or optical processors which can execute all the steps required of it, or any hardware or software combination which will perform those or equivalent steps, such as one or more general purpose digital microprocessors suitably programmed from a computer readable medium carrying necessary program code. Any "memory" includes any suitable device or combination of devices in which a processor can store and/or retrieve data as required, such as magnetic, optical, or solid state storage devices (including magnetic or optical disks or tape or RAM, or any other suitable device or combination of them, either fixed or portable). Steps recited in a particular order in relation to any method can be performed in that order or changed to any order which is logically possible. Reference to a singular item, includes the possibility that there are plural of the same items present. All patents and other cited references are incorporated into this application by reference.

Figure 2:
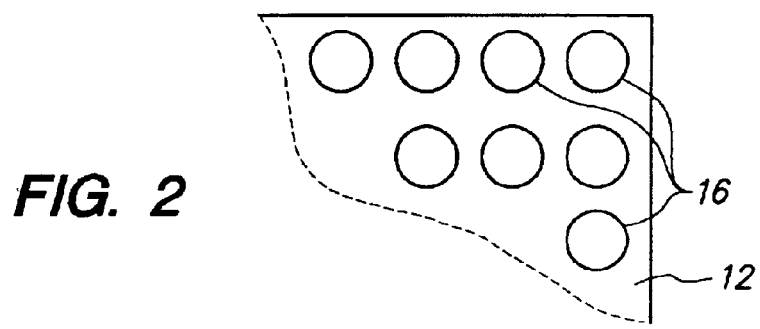
FIG. 2 is an enlarged view of a portion of FIG. 1 showing multiple ideal spots or features.
Figure 3:
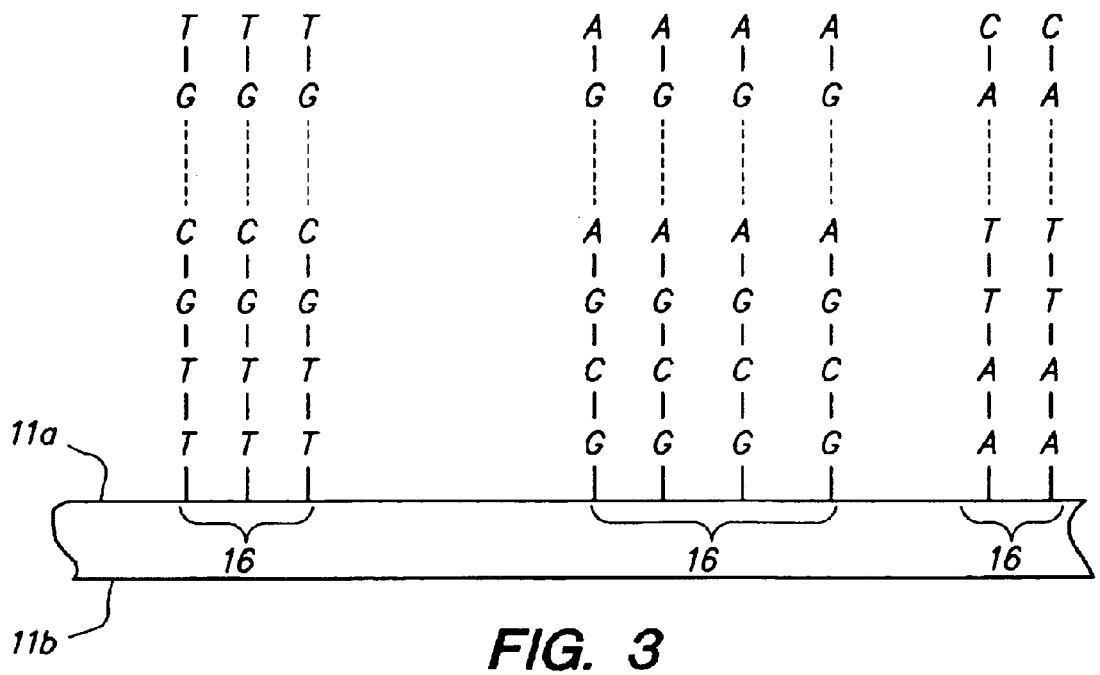
FIG. 3 is an enlarged illustration of a portion of the substrate in FIG. 2.

Referring first to FIGS. 1–3, methods and apparatus of the present invention may generate or use a contiguous planar substrate 10 carrying one or more arrays 12 disposed across a front surface 11a of substrate 10 and separated by inter-array areas 13. A back surface 11b of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). Each array 12 has associated with it a unique identifier in the form of a bar code 356 described below. By "unique" in this sense does not mean the identifier is absolutely unique, but it is sufficiently long so as unlikely to be confused with another identifier on another array (and is preferably unique as to a particular central fabrication station on a given communication channel). While ten arrays 12 are shown in FIG. 1 and the different embodiments described below may use a substrate with only one array 12 on it, it will be understood that substrate 10 and the embodiments to be used with it may have any number of desired arrays 12. Similarly, substrate 10 may be of any shape, and any apparatus used with it adapted accordingly. Depending upon intended use, any of all of arrays 12 may be the same or different from one another and each will contain multiple spots or features 16 of biopolymers such as polynucleotides. A typical array may contain from more than ten, more than one hundred, more than one thousand or ten thousand features, or even more than from one hundred thousand features. All of the features 16 may be different, or some or all could be the same. In the embodiment illustrated, there are interfeature areas 17 between features, which do not carry any polynucleotide. It will be appreciated though, that the interfeature areas 17 could be of various sizes and configurations. It will be appreciated that there need not be any space separating arrays 12 from one another, nor features 16 within an array from one another. However, in the case where arrays 12 are formed by the deposition method as described above, such inter-array and inter-feature areas 17 will typically be present. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

FIGS. 2 and 3 are enlarged views illustrating portions of ideal features where the actual features formed are the same as the desired features (sometimes referenced as the "target" or "aim" features), with each feature 16 being uniform in shape, size and composition, and the features being regularly spaced. In practice, such an ideal result is difficult to obtain.

Figure 4:
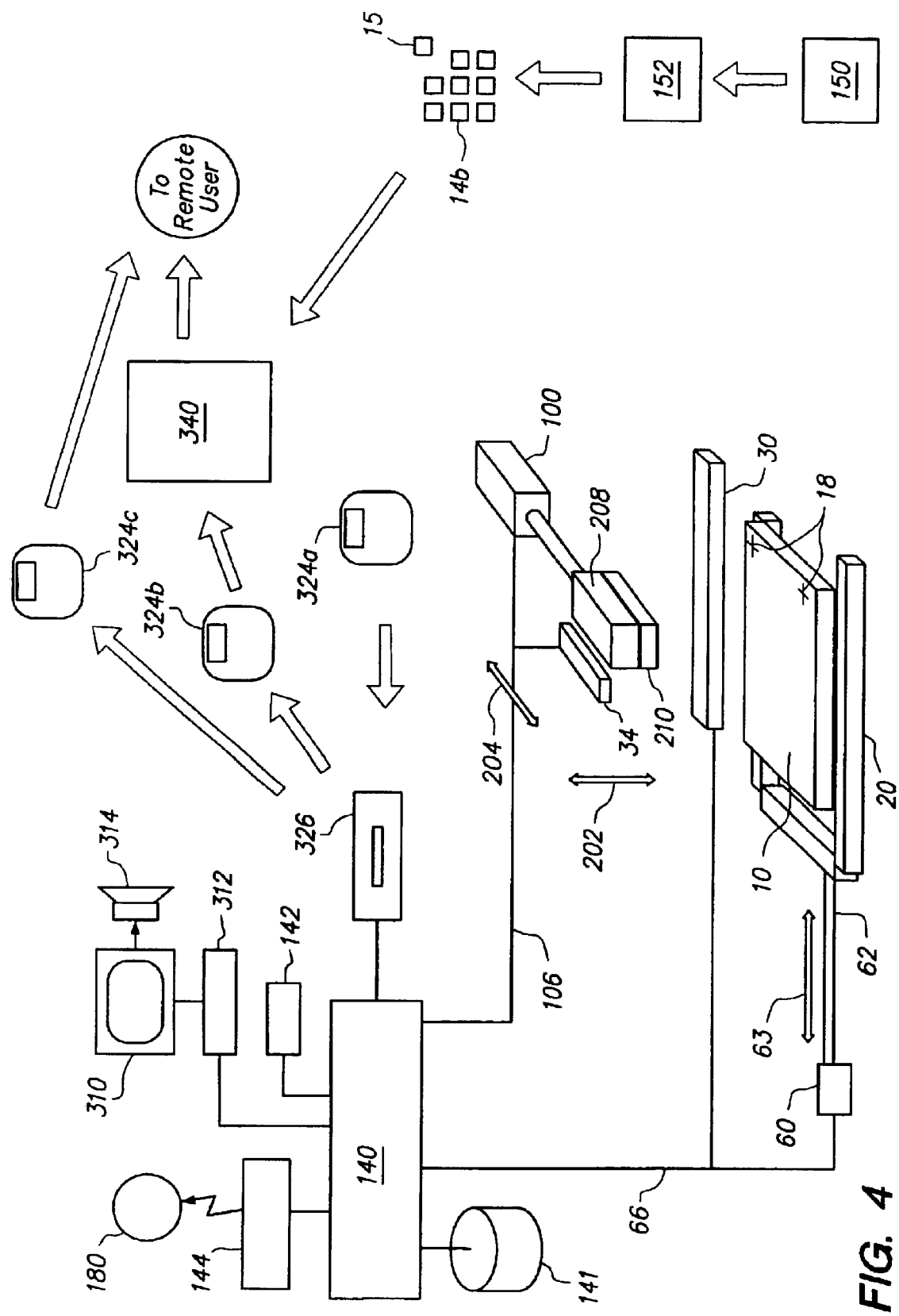
FIG. 4 is a schematic diagram of an apparatus of the present invention in the form of a central fabrication station.

Referring now to FIG. 4, an apparatus of the present invention which can execute a method of the present invention, will now be described. The apparatus of FIG. 4 is a central fabrication station which includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 10 without exerting too much pressure thereon, since substrate 14 is often made of glass.

A dispensing head 210 is retained by a head retainer 208. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 63 is provided by transporter 60. In the case where arrays 12 are to be fabricated by the deposition method, transporter 60 can also move a load station (not shown) beneath head 210 such that polynucleotides or other biopolymers obtained from different vessels from a customer, can be loaded into head 210. Such a load station and method of use is described in detail in U.S. patent application Ser. No. 09/183,604 for "Method And Apparatus For Liquid Transfer" filed Oct. 30, 1998 by Tella et al, incorporated herein by reference. In the case where arrays 12 are to be fabricated by the in situ method, supplies of suitable reagents can be provided in fluid communication with head 210, and a flood station can be provided for steps in the process in which all features to be formed are exposed to the same solution. Such features are described in more detail in U.S. patent application Ser. No. 09/356,249 for "Biopolymer Arrays And Their Fabrication" filed by Perbost on Jul. 16, 1999, incorporated herein by reference. Head 210 may also optionally be moved in a vertical direction 202, by another suitable transporter (not shown). It will be appreciated that other scanning configurations could be used. It will also be appreciated that both transporters 60 and 100, or either one of them, with suitable construction, could be used to perform the foregoing scanning of head 210 with respect to substrate 10. Thus, when the present application recites "positioning" one element (such as head 210) in relation to another element (such as one of the stations 20 or substrate 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Processor 140 also has access through a communication module 144 to a communication channel 180 to communicate with one or more remote stations, such as locations at which arrays 12 are read. Communication channel 180 may, for example, be a Wide Area Network ("WAN"), telephone network, satellite network, or any other suitable communication channel. Communication module 144 may be any module suitable for the type of communication channel used, such as a computer network card, a computer fax card or machine, or a telephone or satellite modem.

Head 210 may have multiple pulse jets, such as piezoelectric or thermoelectric type pulse jets as may be commonly used in an ink jet type of printer and may, for example, include multiple chambers each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. A suitable head construction is described in U.S. patent application Ser. No. 09/150,507 filed Sep. 9, 1998 by Caren et al. for "Method And Multiple Reservoir Apparatus For Fabrication Of Biomolecular Arrays", incorporated herein by reference. Alternatively, multiple heads could be used instead of a single head 210, each being similar in construction to head 210 and being movable in unison by the same transporter or being provided with respective transporters under control of processor 140 for independent movement.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation of display 310 and speaker 314. Memory 141 may be any suitable device or devices in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required for by the present invention for array production, or any hardware or software combination which will perform those or equivalent steps. The programming can be provided remotely to processor 140, or previously saved in a computer program product such as memory 141 or some other portable or fixed computer readable storage medium using any of those devices mentioned below in connection with memory 141. For example, a magnetic or optical disk 324a may carry the programming, and can be read by disk writer/reader 326.

A writing system which is under the control of processor 140, includes a writer in the form of a printer 150 which applies identifiers onto substrate 10 by printing them in the form of the bar codes 356 directly onto substrate 10 (or indirectly such as onto a label later attached to the substrate), each in association with a corresponding array 12 as illustrated in FIG. 1. Alternatively, the identifiers can by applied onto a housing carrying the substrate or label to be applied to such substrate or housing. Printer 150 may accomplish this task before or after formation of the array by the drop deposition system. The identifiers may include a communication address which can identify to a location (such as an end user station) an address of a remote location on communication channel 180 from which will be communicated first and/or update sets of feature characteristic data for an array in response to a received communication of the identifier for that array or, where the feature characteristic data is biopolymer function data of the identifier or identity information of one or more biopolymers on that array. As mentioned, such feature characteristic data may include feature physical characteristics or biological function data for one or more of the biopolymers on array features. Such location will have a memory accessible on the communication channel 180 carrying a database of the data in association with corresponding array identifiers or corresponding biopolymer identity information so as to facilitate retrieval of the data upon receipt of the array identifier or biopolymer identity information. The location identified by the communication address may be that of communication module 144 or alternatively that of another location. Examples of a communication address may be a telephone number, computer ID on a WAN, or an internet Universal Resource Locator. The writing system further includes a data writer/reader 326 (such as an optical or magnetic disk drive) which can write data to a portable computer readable storage medium (such as an optical or magnetic disk). A cutter 152 is provided to cut substrate 10 into individual array units 15 each carrying a corresponding array 12 and bar code 356.

Figure 5:
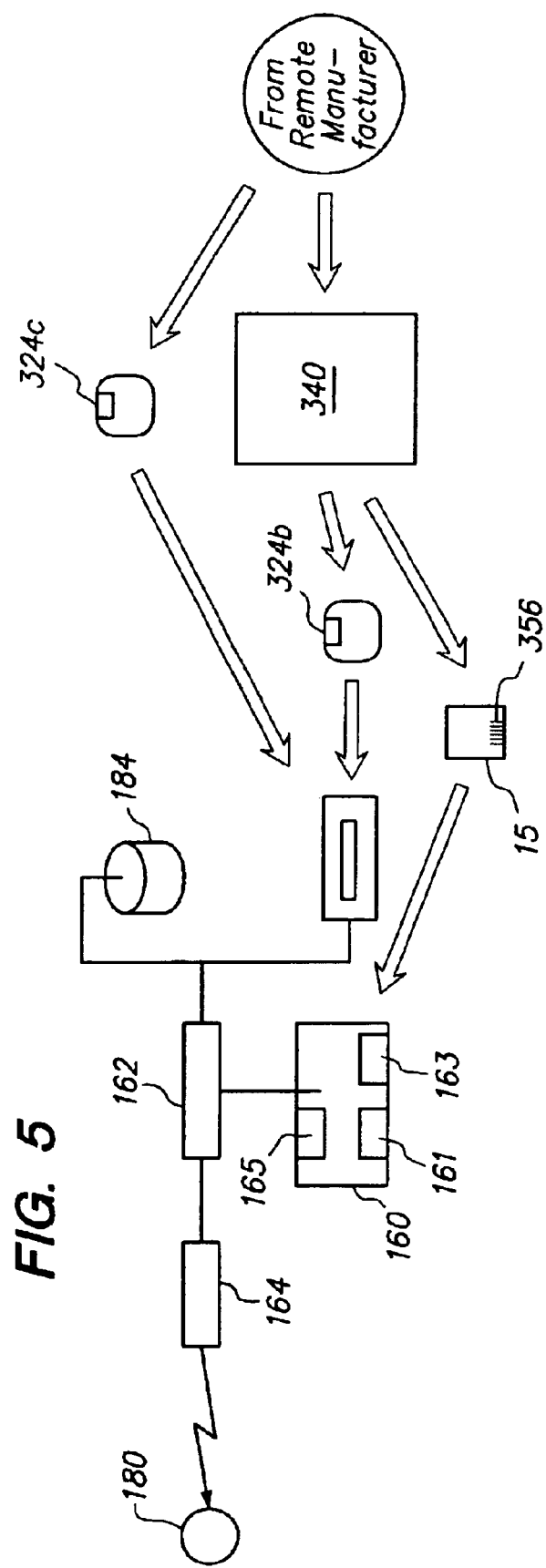
FIG. 5 is a schematic diagram of an apparatus at a user site which can execute a method of the present invention.

FIG. 5 illustrates an apparatus at which an addressable array 12 may be used, in particular a single "user station" which is remote from the fabrication station (usually at the location of the customer which ordered a received array 12). The user station includes a processor 162, a memory 184, an array reader in the form of a scanner 160 to read an array following exposure to a sample, data writer/reader 186 (which may be capable of writing/reading to the same type of media as writer/reader 320), and a communication module 164 which also has access to communication channel 180. Scanner 160 may include a holder 161 which receives and holds an array unit 15, as well as a source of illumination (such as a laser) and a light sensor 165 to read fluorescent light signals from respective features on the array. Communication module 164 may be any type of suitable communication module, such as those described in connection with communication module 144. Memory 184 can be any type of memory such as those used for memory 141. Scanner 160 can be any suitable apparatus for reading an array, such as one which can read the location and intensity of fluorescence at each feature of an array following exposure to a fluorescently labeled sample. For example, such a scanner may be similar to the GENEARRAY scanner available from Hewlett-Packard, Palo Alto, Calif. Scanner 160 also includes though, a reader 163 to read the identifier in the form bar code 356 appearing on segment 15 as a read identifier signal. However, less preferably this reader may be the same as the array reader. The scanning components of scanner 160, holder 161, and reader 163 may all be contained within the same housing of a single same apparatus.

It will be understood that there may be multiple such user stations, each remote from the fabrication station and each other, with the fabrication station of FIG. 4 acting as a central fabrication station (that is, a fabrication station which services more than one remote user station at the same or different times). One or more such user stations may be in communication with the fabrication station at any given time. It will also be appreciated that processors 140 and 162 can be programmed from any computer readable medium carrying a suitable computer program. For example, such a medium can be any memory device such as those described in connection with memory 141, and may be read locally (such as by reader/writer 320 in the case of processor 140 or writer/reader 186 in the case of processor 162) or from a remote location through communication channel 180.

Figure 6:
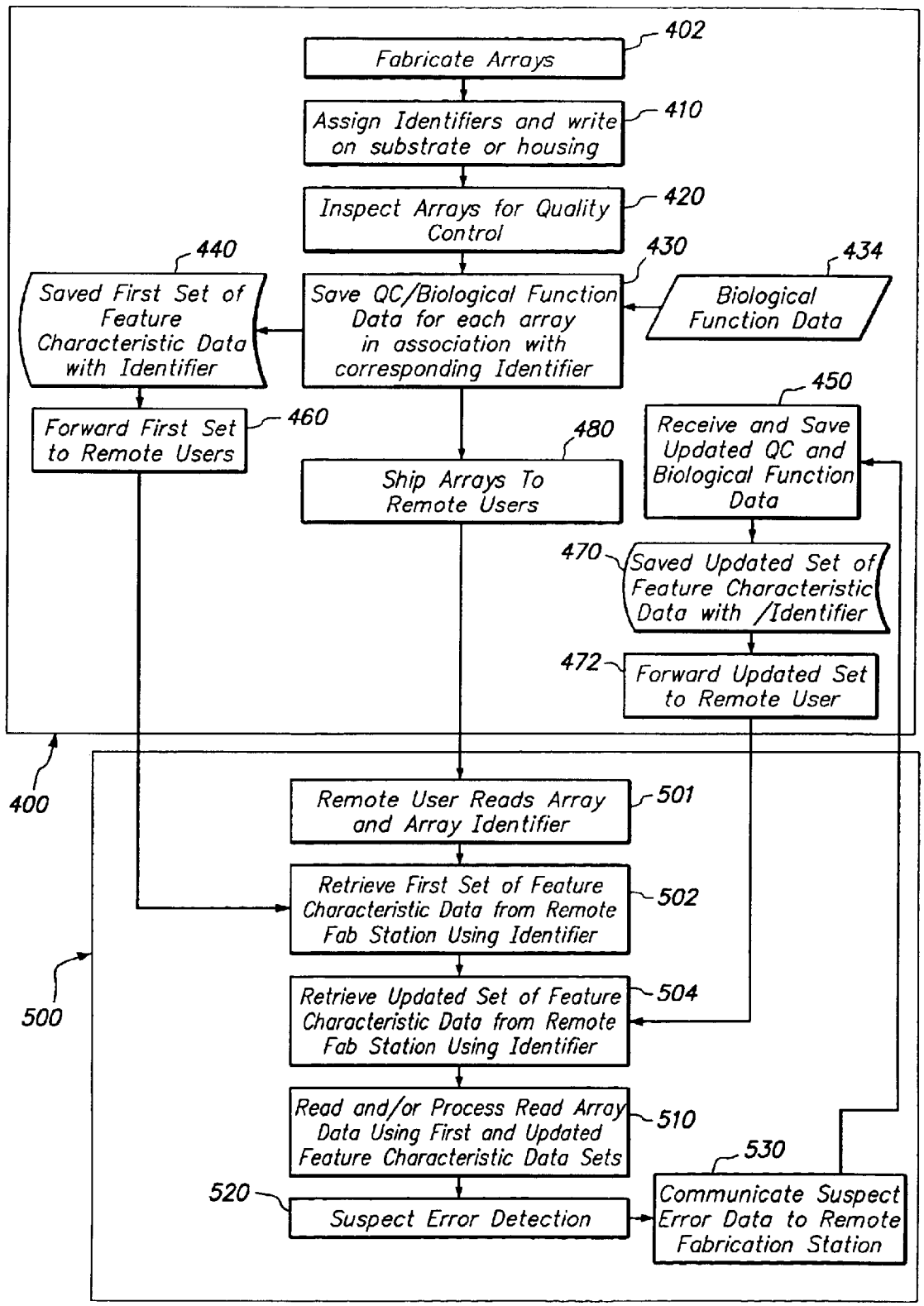
FIG. 6 is a flowchart illustrating methods of the present invention.

The operation of the fabrication station will now be described with reference to FIGS. 4 and 6. Reference numbers appearing in FIG. 6 are shown in parentheses, with events at the central fabrication station being within box 400 and those at a single user station within box 500. Events for only one user station remote from the central fabrication station are shown in FIG. 6, but it will be understood that typically there will be many such remote user stations. It will be assumed that a substrate 10 on which arrays 12 are to be fabricated, is in position on station 20 and that processor 140 is programmed with the necessary layout information to fabricate target arrays 12. Processor 140 controls fabrication of each array by depositing one or more drops of each biopolymer onto a corresponding region (feature) on the substrate in the case of the deposition method, or by depositing biomonomer drops onto a region and sending the array to the flood station in the case of the in situ method, so as to fabricate the array (400). During or following array fabrication, arrays are inspected for quality control ("QC") (420), for example for information on missing features, misplaced features, features of incorrect dimensions, or other physical characteristics, in a manner as described in U.S. patent application Ser. No. 09/302,898 for "Polynucleotide Array Fabrication" filed Apr. 30, 1999 by Caren et al., and application Ser. No. 09/419,447 for "Biopolymer Array Inspection" filed Oct. 15, 1999 by Fisher, both incorporated herein by reference. Available biological function data (434) for biopolymers on the array is retrieved by processor 140 using biopolymer identity information (such as sequence information) from portable storage medium 324a and/or from one or more remote databases through communication channel 180. "Biological function data" includes any biological information on an array feature or a target, such as information on the function of a target (such as cDNA) or its complement (such as the mRNA from which the cDNA was derived), or the gene from which either originated directly or indirectly (such as the gene from which the mRNA complementary to a target cDNA, was transcribed). For example, biological function data may include information such as a gene identification (for example, a gene name) or function from which is transcribed mRNA the DNA complement of which is detected by a particular feature or features. Any other information which might be of use to the end user may be forwarded in addition to, or instead of, the biological function data. Any such information includes information which is associated with an array and may be used by the user in reading that array or processing results read from the array (such as information on where to obtain further information on the array layout or processing of read results).

For each fabricated array 12, processor 140 will generate a corresponding unique identifier and will save (430) this in memory 141 in association with the following (together forming a first set of feature characteristic data 440): target array layout information (including the location and identity of biopolymers at each feature); quality control data (obtained in step 420); and biological function data (434). Either before array fabrication on substrate 10 has been commenced, or after it has been completed, substrate 10 may be sent to writer 150 which, under control of processor 140, writes (410) the identifier for each array 12 in the form of bar codes 356 onto substrate 10 each in association with its corresponding array (by being physically close to it in the manner shown in FIG. 1). The substrate 10 is then sent to a cutter 152 wherein portions of substrate 10 carrying an individual array 12 and its associated local identifier 356 are separated from the remainder of substrate 10, to provide multiple array units 15. The array unit 15 is placed in package 340 along with storage medium 324b (if used) carrying the first set of feature characteristic data and identifier for that same array unit 15 (and possibly for other array units 15 which are to be sent to the same remote customer location), and the package then shipped (480) to a remote user station. The first set of feature characteristic data 440 for each such array is forwarded (460) to the same remote users, either by shipping to each user in association with the corresponding array identifier on portable storage medium 324b, or by communicating the first set over channel 180 in response to a received communication from the remote station of the corresponding array identifier. An identification of the features in the array to which any data pertains, is included as a part of the feature characteristic data. Note that the feature characteristic data may only be for a sub-set of features on a given array. Alternatively, in the less desired situation where the first set carries only biological function data, biopolymer identifications may be used in place of the array identifier.

At some time after fabrication of an array (for example, after it has been shipped to a remote user), the fabrication station may receive (450) further array quality control and/or biopolymer biological function data from various sources. For example, such may be received from a remote array user as illustrated in FIG. 6 and described below. However, such may additionally be received as a result of the fabricator's own investigations or from remote databases. For example, quality data (such as an error in the placement, dimensions, or presence) of one or more features may be discovered by an individual at the fabrication station by later inspection of some arrays of a same feature pattern made in a same batch as other arrays previously shipped to one or more customers. Additionally, biological function data may be automatically retrieved by processor 140 at predetermined time intervals from one or more remote databases over communication channel 180 using data on the identity of the biopolymers on previously fabricated arrays 12 which was saved in memory 141. Any further such received quality or biological function data is saved (470) in memory 141 in association with the corresponding array identifier for later forwarding (472) to one or more remote user stations (any one or more of which may be the same or different from the remote user that provided all or part of such further data).

The above sequence can be repeated at the fabrication station as desired for multiple substrates 10 in turn. As mentioned above, the fabrication station may act as a central fabrication station for each of multiple remote user stations, in the same manner as described above. Whether or not the fabrication station acts as a central fabrication station, it can optionally maintain a database of the first sets of feature characteristic data (and update sets), each in association with the corresponding array identifier. However, such database can be maintained at another location and may be dispensed with in the case where the first sets are shipped on portable storage media (such as medium 324b) to the end users.

At the user station of FIG. 5, the resulting package 340 is then received from the remote fabrication station. A sample, for example a test sample, is exposed to the array 12 on the array unit 15 received in package 340. Following hybridization and washing in a known manner, the array unit 15 is then inserted into holder 161 in scanner 160 for reading of the array (such as information representing the fluorescence pattern on the array 12). The array identifier is also machine read by the reader 163 in scanner 160 reading (501) the bar code 356 present on the array substrate 10 in association with the corresponding array 12, while the array unit 15 is still positioned in retained in holder 161. Using read identifier 356 (or biopolymer identification information), processor 162 may then retrieve (502) the first set of feature characteristic data for the array either from portable storage medium 324b or from the database of such information in memory 141 by communicating the array identifier to that database through communication module 164 and communication channel 180 and receiving the corresponding first set of feature characteristic data in response. In the latter situation, processor 162 may obtain the communication address of communication module 144 by which to access memory 141 (or the address of another database carrying the identity map and associated identifier of array 12), from a communication address in identifier 356 or by accessing a database of manufacturer's communication addresses based on the read array identifier (either from a local memory or by communication with a remote database). Processor 162 may retrieve (504) the updated set of feature characteristic data (470) in any of the same ways the first set of feature characteristic data is obtained, although this may be obtained at the same, earlier, or later time. The retrieved first and updated sets may optionally be merged by replacing feature characteristic data from the first set for a given feature with corresponding data from the update set when the first set data conflicts with the updated set data. For example, if the first set indicates a particular feature is present and the updated set indicates that it is not, the merged data indicates that feature is not present. Thus, when use of the first and updated sets is referenced in reading or processing read data from the array, this may be done by way of using the merged data.

The array in array unit 15, while still positioned in holder 161, may be read to obtain read results. Processor 162 may cause the array to be read, or the data obtained from reading to be processed (which term includes interpretation of data), (510) using the retrieved first and updated feature characteristic sets. For example, if the sets together indicate a particular feature is missing or severely defective then the scanner may simply avoid reading such a feature at all. Alternatively, the read data from such a feature may simply be deleted or ignored in any subsequent processing, or processed results flagged as possibly being in error due to that defective feature. As mentioned, the first and/or updated sets may include biopolymer identification information, and this can also be used to retrieve an additional updated set of array feature characteristic data from one or more other local or remote locations (by communication of the biopolymer identifications and receiving in response, the updated set). Results from the array reading can be processed results, such as obtained by rejecting a reading for a feature which is below a predetermined threshold and/or forming conclusions based on the pattern read from the array (such as whether or not a particular target sequence may have been present in the sample). The results of the reading (processed or not) can be forwarded (such as by communication) to be received at a remote location for further evaluation and/or processing, or use, using communication channel 180 or reader/writer 186 and medium 190. This data may be transmitted by others as required to reach the remote location, or re-transmitted to elsewhere as desired.

During array reading or processing read data, a suspected error in a feature characteristic (such as presence, placement, dimensions, or biopolymer concentration) may be detected (520). The suspected error can then be communicated (530) to the remote fabrication station in association with the corresponding array identifier or biopolymer identity data, where such information may optionally be analyzed and, if considered appropriate (for example, where the same suspected error for an array of a same feature pattern is reported by multiple remote users) added to the updated set of feature characteristic data. Alternatively or additionally, further biological function data for a feature may be communicated to the fabrication station for adding to the updated set. Such further updated set is then available for retrieval by the same or other remote users. In this manner, multiple remote users can contribute to the continuous improvement in the updated feature characteristic set.

In a variation of the above, it is possible that each array 12 and its substrate 10 may be contained with a suitable housing. Such a housing may include a closed chamber accessible through one or more ports normally closed by septa, which carries the substrate 10. In this case, the identifier for each array may be applied to the housing.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface(for example, a series of concentric circles or semi-circles of spots), and the like. Even irregular arrangements of the arrays or the regions within them can be used provided the locations of features of identified biopolymers are known. Further, the identifier shipped to a remote user with the array need not be on the array substrate or housing provided it is in some manner associated with the corresponding array when shipped to the user. For example, the identifier could be only on portable storage medium 324b or a paper or other printed medium which is associated with the corresponding array such as by being physically associated with it in the same package 340.

The present methods and apparatus may be used to deposit biopolymers or other moieties on surfaces of any of a variety of different substrates, including both flexible and rigid substrates. Thus, in any of the above described methods "biopolymer" or "biopolymers" could more broadly be replaced with "moiety" or "moieties". Preferred materials for the substrate provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be porous or non-porous, smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various further modifications to the particular embodiments described above are, of course, possible. Accordingly, the present invention is not limited to the particular embodiments described in detail above.

What is claimed is:

1. A method of using an addressable array of biopolymers on a substrate, comprising:
   (a) receiving an array of addressable biopolymer regions and an associated machine readable identifier carried on an array substrate or array housing;
   (b) exposing the array to a sample;
   (c) reading the array;
   (d) machine reading the identifier as an identifier signal; and
   (e) retrieving updated biological function data for one or more of the biopolymers from a memory based on the identifier signal, wherein the retrieved biological function data comprises information on the function of a target of the array, or its complement, or the gene from which either originated;
   wherein the retrieval of the biological function data includes: communicating the identifier signal to a processor which retrieves data on the identity of the biopolymers based on the read identifier, and communicating the identity data on the biopolymers to a processor which retrieves the biological function data for one or more of the biopolymers from a memory based on the retrieved identity data.

2. A method according to claim 1 wherein the biopolymers are polynucleotides.

3. A method according to claim 2 wherein the biopolymers are DNA.

4. A method according to claim 1 wherein the memory from which biological function data is retrieved is a portable storage medium received from a remote location.

5. A method according to claim 4 wherein the machine readable identifier is read while the array is in a same apparatus which reads the array.

6. A method according to claim 1 wherein the processor which retrieves the biological function data and the memory from which the biological function data is retrieved, are remote from the location at which the array and identifier are read, and wherein the read identifier or identity data is communicated to the remote processor.

7. A method according to claim 1 wherein the retrieved biological function data comprises information on the gene from which a target or its complement originated.

8. A method according to claim 7 wherein the biopolymers are polynucleotides.

9. A method according to claim 1 wherein the retrieved biological function data comprises information on the gene from which a target of the array, or its complement, originated.

10. A method of using an addressable array of biopolymers on a substrate, comprising:

(a) receiving an array of addressable biopolymer regions and an associated machine readable identifier carried on an array substrate or array housing;

(b) exposing the array to a sample;

(c) reading the array;

(d) machine reading the identifier as an identifier signal; and (e) communicating with a remote station and retrieving therefrom updated biological function data for one or more of the biopolymers based on the identifier signal, wherein the retrieved biological function data comprises information on the function of a target of the array, or its complement, or the gene from which either originated, wherein the retrieval of the biological function data includes: communicating the identifier signal to a processor which retrieves data on the identity of the biopolymers based on the read identifier; and communicating the identity data on the biopolymers to a processor which retrieves the biological function data for one or more of the biopolymers from a memory based on the retrieved identity data.

11. A method according to claim 10 wherein the biological function data is retrieved by communicating to the remote station the identifier signal, or communicating to the remote station, biopolymer identity obtained using the identifier signal, and receiving the biological function data in response.

12. A method according to claim 11 additionally comprising:

obtaining a communication address of the remote station using the identifier signal;

wherein the communication address is used to establish communication with the remote station.

13. A method according to claim 11 additionally comprising retrieving the biopolymer identity data from a memory carrying multiple identifiers in association with the biopolymer identity data, using the identifier signal, and wherein the biopolymer identity data is communicated to the remote station to retrieve the biological function data in response.

14. A method according to claim 10 wherein the biopolymers are polynucleotides.

* * * * *